United States Patent [19]
Essen-Möller

[11] Patent Number: 5,981,951
[45] Date of Patent: Nov. 9, 1999

[54] METHOD AND A SYSTEM FOR DETERMINATION OF COMPONENTS OF A SUBSTANCE

[75] Inventor: Anders Essen-Möller, Stockholm, Sweden

[73] Assignee: Diamyd Medical Aktiebolag, Stockholm, Sweden

[21] Appl. No.: 08/913,135

[22] PCT Filed: Mar. 13, 1996

[86] PCT No.: PCT/SE96/00327

§ 371 Date: Nov. 4, 1997

§ 102(e) Date: Nov. 4, 1997

[87] PCT Pub. No.: WO96/28720

PCT Pub. Date: Sep. 19, 1996

[30] Foreign Application Priority Data

Mar. 13, 1995 [SE] Sweden .................................. 9500893

[51] Int. Cl.⁶ .............................. G01N 21/01; G01J 1/58
[52] U.S. Cl. ................ 250/341.1; 250/343; 250/339.12; 250/339.11
[58] Field of Search ................... 250/341.1, 343, 250/339.12, 339.11

[56] References Cited

U.S. PATENT DOCUMENTS

| 4,309,112 | 1/1982 | Ashley et al. . |
| 4,855,930 | 8/1989 | Chao et al. . |
| 5,077,476 | 12/1991 | Rosenthal ................................ 250/341 |

FOREIGN PATENT DOCUMENTS

| 160768 | 5/1984 | European Pat. Off. . |
| 9118548 | 12/1991 | WIPO . |

*Primary Examiner*—Constantine Hannaher
*Assistant Examiner*—Andrew Israel
*Attorney, Agent, or Firm*—Dowell & Dowell, P.C.

[57] ABSTRACT

A method and system for determining the presence of one or more components in a liquid substance including illumination of the substance utilizing a light with at least one definite wave length preferably within the almost infrared area and detecting transmitted and/or reflected light and analyzing the detected light wherein the detection is performed extremely fast so as to detect a step response corresponding to an approaching or fading light pulse transmitted or reflected through the substance.

18 Claims, 1 Drawing Sheet

METHOD AND A SYSTEM FOR DETERMINATION OF COMPONENTS OF A SUBSTANCE

BACKGROUND OF THE INVENTION

1. Field of the Invention

The present invention relates to a method to determine the presence of one or several components in a e.g. liquid substance by means of spectroscopy including an illumination of the substance with light of at least one wave length and detecting transmitted and/or reflected light as well as analyzing the reflected light characteristics.

The invention also relates to a system for performing the method and an ambulatory registration system.

2. Brief Description of the Related Art

Methods and systems essentially for measuring e.g. the blood sugar content are already known in the art. The known systems use in many cases optical measurements, in which a blood carrying body portion, such as a finger tip, are illuminated with light of several different wave lengths, the transmitted or reflected light then being analyzed by means of differential spectroscopy to distinguish between various components and to define the amount of interesting such ones. In measurements of this known type the measuring accuracy will in many cases be not fully satisfactory and not comparable with analytic measurements.

SUMMARY OF THE INVENTION

The present invention relates to a method and a system offering an increased accuracy during measurements basing on differential spectroscopy in general and especially for noninvasive, to blood compositions related measurements.

Thus, the invention relates to a method according to the first part of the attached claim 1. The method is especially characterized in what is specified in the characterizing part of said claim.

Moreover, the invention relates to a system according to the first part of the attached claim 10. The system is especially characterized in what is specified in the characterizing part of said last mentioned claim.

The invention also relates to an ambulatory registration system according to the first part of the attached claim 15. The system is especially characterized by what is stated in the characterizing part of claim 15.

BRIEF DESCRIPTION OF THE DRAWINGS

The invention is described here below in connection with an execution example and the attached drawing, on which.

DESCRIPTION OF THE PREFERRED EMBODIMENT

Figure 1:
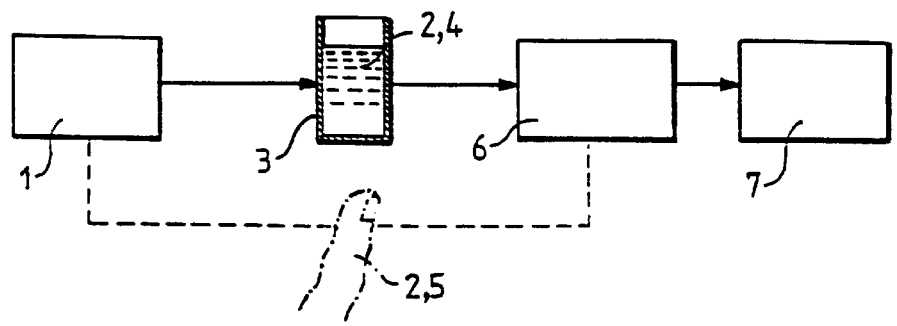
FIG. 1 shows a scheme in principle of a first embodiment of a system according to the invention.
Figure 2:
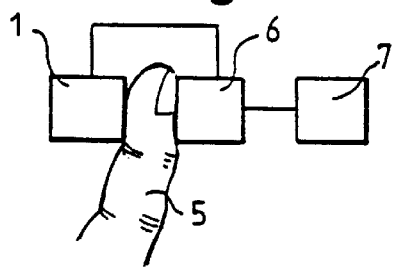
FIG. 2 shows schematically and in more detail a system according to FIG. 1 during a measurement of a finger tip.

In FIG. 1 item 1 designates devices to illuminate a substance 2 arranged with a within a vessel 3 comprized liquid 4, and as an alternative a finger tip 5 with light of at least one well defined wave length, but preferably a multiple of well defined wave lengths, at least some wave lengths preferably lying within the almost infrared area. Item 6 designates devices for detecting transmitted and/or reflected light, to varying extent passing through the substance and thereby being effected by means of absorption in the substance, the absorption being related to wave length and substance. Item 7 designates devices for analyzing detected light in relation to light approaching the substance by means of a method of spectroscopy, generally called differential spectroscopy, where several wave lengths are used. This kind of technology is already known in the art and is described in U.S. Pat. No. 5,222,495.

According to the present invention devices are provided for determining completing characteristics besides the mere absorption determination.

Figure 3:
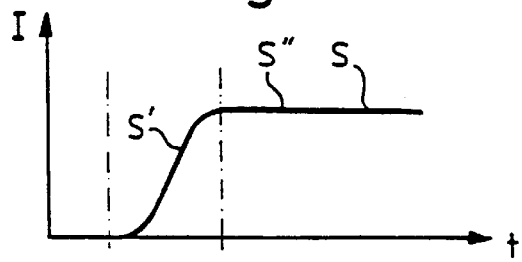
FIG. 3 shows schematically a step response for a system according to FIG. 1.

According to a first embodiment, the detecting devices are adapted to define extremely fast processes, i.e. to detect during extremely short time periods, so that a detailed step response corresponding to an approaching light pulse might be determined in the way as it is principally shown in FIG. 3, the detected intensity there being illustrated as a function of the time t.

Figure 4:
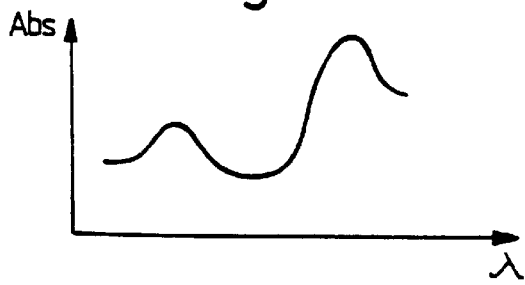
FIG. 4 shows schematically the light absorption for various wave lengths.

The correlation between intensity and time thereby comprizes a step response S' and a steady portion S" corresponding to a continuous illumination. The step response portion shows in its left part, the in time first part, the intensity for light having passed by the shortest way through the substance 2, whereas in time later parts of both the step response portion and the steady portion correspond to light having passed the substance by differently long ways. The portion S' corresponds to known measurements, the intensity level of this portion corresponding to a point in the absorption/wave length-diagram. FIG. 4, of a known type. The step response portion S' is during its course in many cases both depending of the substance and the wave length and is according to the invention adapted to be used s a completing information for distinguishing various components of the substance and for a quantity determination of the presence of a certain component, the analysis of detected light being achieved in relation to previous step responses being fixd under well defined conditions. For various points of correlation as depicted in FIG. 4 also a characterizing step response might be defined and used to analyze detected light.

Figure 5:
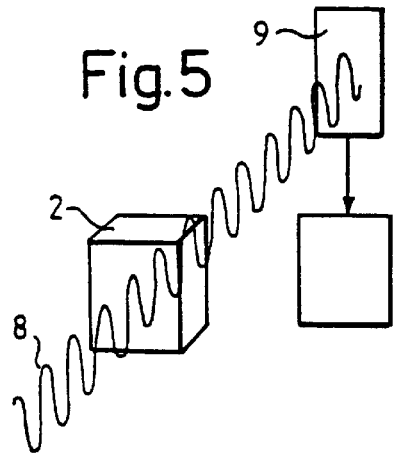
FIG. 5 shows schematically the rotation of a plane-polarized beam of rays and a detection.

According to a second embodiment the plane-polarized light 8, FIG. 5, is used to illuminate the substance, devices 1 being adapted to generate plane-polarized light and the fact being used, that certain components, such as glucose in the blood, are turning the plane-polarized light as scheamtically illustrated in FIG. 5. Detecting devices 9 are provided for detecting the light thus turned, the amount of said turning being related to both substance and wave length, which are used for an analysis for distinguishing various components in the substance and a quantity definition of the presence of a certain component with the described turning capacity.

Also embodiments might be envisaged as combinations of said first and said second embodiment.

According to embodiments preferred in certain cases embodiments (not shown) are provided to supply a varying and/or steady electrical and/or magnetic field across the substance, the dipole moment of certain component molecules being influenced, the detected light characteristics thus being influenced and said influence being used to distinguish various components and for quantity analysis of the presence of certain components.

As for embodiments for plane-polarized light devices 1 are provided for generating plane-polarized light with at least one wave length and to combine this with a light with at least one reference wave length and with a light with at least one measuring wave length. During this analysis the angle distortion of the plane-polarized light is adapted to be related to the characteristics of a transmitted and/or reflected light by means of a reference and a measuring wave length.

The invention can be applied to determine and measure all kind of solid, liquid and gaseous substances.

Figure 6:
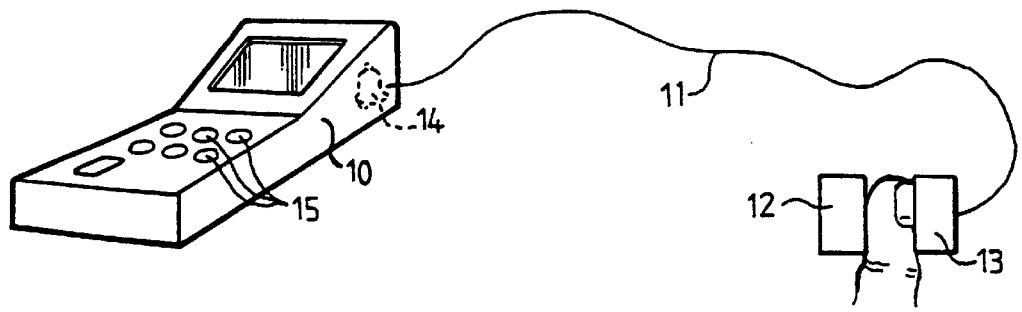
FIG. 6 shows schematically an ambulatory registration system according to the invention.

According to a preferred application the invention is adapted to be used for mainly a noninvasive determination of the blood glucose contents in human beings, such as individuals with diabetes. The invention combined with an ambulatory registration of the blood sugar contents, FIG. 6, is here a new and extraordinarily suitable method and system compared with already known ones. Item 10 designates a digital registration unit adapted for an ambulatory use connected to a blood-sugar-sensor adapted to be placed onto an individual. The connection 11 can be electrical and/or fibreoptical or be wireless, e.g. telemetric or infrared based. Said sensors are also preferably optical as above mentioned and preferably noninvasive.

The unit 10 is thus further combined with illumination elements 12 and detecting elements 13, at least one of these elements possibly being included in the unit. Both kind of elements might also be external. According to an embodiment the unit has an alarm function 14 to be triggered of the defined glucose content, an alarm then being triggered, when the content passes over a previously defined level and/or when the content passes below a previously defined level.

It is preferred that the unit comprises a registrating capacity of at least 8 hours and is equipped with symptom and event controls 15 so that the registration might be supplemented with data on events, such as intake of food and medicine, and symptoms. Moreover, the unit is preferably and simultaneously adapted for a registration of one or several parameters out of the group consisting of EGG, pulse, conductivity, EEG, eye movement, respiration, leg movement, reflex, percentage $SaO_2$, urea, albumin, cholesterol, etc.

Preferably, the unit is also adapted to communicate with a computer or printer to substantiate the registered information in form of a report (not shown). It is also preferred that the unit is adapted so that information can be transmitted directly to a patients records, e.g. Synectics Polygram for Windows or similar (not shown).

An ambulatory unit of the type previously described might also be used in connection with an invasive recording (not shown) of the blood-sugar-content. Sensors might then be based on deoxyhydrogenase. According to an embodiment the sensor is situated outside of the measuring place, e.g. in a microdialyse system.

The method as well as the function of the system according to the invention should be essentially evident from what is stated above. The basis are known principles for spectroscopic detection of transmitted and/or reflected light of at least one defined wave length and of the analysis of the absorption characteristics. In using extremely fast detection over extremely short periods the characteristic step response is determined and by using plane-polarized light the characteristic angle distorsions are evaluated. Thus, the obtained information supplements already known absorption determinations and the analysis basing on such determinations as to the quality and quantity presence and enables more exact determinations and even determinations of a new kind.

As also is evident from what was, stated above, the invention provides essential advantages compared with what is known in the art. Such an advantage, being of course very important in a medical respect, is the increased accuracy, when further information is obtained by means of the invention. In connection with the extremely fast detection the measuring result is reflecting a momentary state and not an average state prevailing during a longer period. The invention provides a noninvasive determination with thereto related advantages and new and important possible applications.

The invention has previously been described in connection with execution examples. Further embodiments might of course be envisaged as well as minor changes and amplifications without leaving the scope of the invention.

Thus, the determination might be provided at various wave lengths passing the substance in question for establishing further important information, as the step responses can be studied by means of the invention.

Moreover, embodiments might be envisaged, where a constant and/or changing electrical and/or magnetic field is applied as a supplementing measurement without the use of an extremely fast detection and the detection of the planpolarized light angle distortion. Various combinations of two or three of these process steps might also be envisaged.

Embodiments might also be envisaged with a detecting of approaching light not necessarily being provided extremely fast, but sufficiently fast, so that the measurement object, the substance, might be regarded being steady, i.e. that molecules, in adaptable cases, the red blood cells, etc., are stationary during an actual measurement. For this purpose such a fast measurement is not necessarily required for obtaining a step response, but only so fast, that nothing might be changed in the measurement area. For an extremely fast measurement time periods of the magnitude of picoseconds are applicable.

Embodiments might also be envisaged with a step response provided, in that the light pulse is terminated, the step response then being an illustration of the progress, how the pulse is fading from a stationary level S" down to an intensity, e.g. zero, corresponding to that no light pulse is prevailing, possibly being illustrated by a progress from the right to the left along the time axis in FIG. 3.

Thus the invention is considered not to be limited to the embodiments specified above and can be modified within the scope provided by the attached claims.

I claim:

1. A method to determine the presence of at least one component in a liquid substance by means of spectroscopy comprising the steps of illuminating the substance by means of light with at least one definite wave length within the almost infrared wave length area and detecting transmitted and/or reflected light and analyzing the detected light characteristics, said detecting being performed during an extremely short time period such that a step response corresponding to an approaching or fading light pulse passing through the liquid substance is detected.

2. A method according to claim 1
   wherein the step of illuminating includes directing a plane-polarized light through the substance and detecting the plane-polarized light angle distortion.

3. A method according to claim 2, wherein the substance is blood, the blood-glucose-contents then being determined.

4. A method according to claim 2, wherein the determination relates to a substance in the human body and is non-invasive.

5. A method according to claim 4, including passing various wave lengths through the substance.

6. The method of claim 2 including applying an electrical and/or magnetic field over the substance during said detection.

7. A method according to claim 6 wherein said period of time is such that the at least one component of the substance is effectively substantially stationary.

8. A method according to claim 1 wherein said period of time is such that the at least one component of the substance is effectively substantially stationary.

9. A method according to claim 1, wherein the light has at least two wave lengths and said detection is by means of differential spectroscopy.

10. A method according to claim 1, wherein the substance is blood, the blood-glucose-contents then being determined.

11. A method according to claim 1, the determination relates to a substance in the human body and is non-invasive.

12. A method according to claim 1, including passing various wave lengths through the substance.

13. A system to determine the presence of at least one component in a liquid substance by means of spectroscopy including means for illuminating the substance with light with at least one wave length within the almost infrared wave length area, and means for detecting transmitted and/or reflected light and means for analyzing detected light characteristics, the improvement comprising said means for detecting including means for detecting a step response corresponding to an approaching or fading light pulse passing through the liquid substance during a short period of time.

14. A system according to claim 10 including means for applying an electrical and/or magnetic field over the substance during said detecting.

15. A system according to claim 14, wherein said means for detecting are non-invasive.

16. A system according to claim 15, wherein said substance is blood, the presence of glucose being determined.

17. A system according to claim 13, wherein said means for detecting detect at least two different wave lengths by means of differential spectroscopy.

18. A system according to claim 13 wherein said means for illuminating includes means for generating plane-polarized light through the substance.

* * * * *